United States Patent [19]
> Grossman et al.

[11] Patent Number: 4,976,960
[45] Date of Patent: Dec. 11, 1990

[54] FOOD SUPPLEMENTS

[75] Inventors: Shlomo Grossman; Michael Albeck, both of Ramat Gan, Israel

[73] Assignee: Bar Ilan University, Ramat Gan, Israel

[21] Appl. No.: 104,419

[22] Filed: Oct. 2, 1987

[30] Foreign Application Priority Data

Oct. 17, 1986 [IL] Israel ................................. 80351
Nov. 26, 1986 [IL] Israel ................................. 80783

[51] Int. Cl.$^5$ ............................................. A61K 35/78
[52] U.S. Cl. ............................. 424/195.1; 424/451;
424/464; 424/600; 514/251; 514/276; 514/458;
514/474; 514/558
[58] Field of Search ................................. 424/195.1

[56] References Cited

U.S. PATENT DOCUMENTS

| | | | |
|---|---|---|---|
| 2,098,254 | 11/1937 | Mattill et al. | 426/546 |
| 2,282,808 | 5/1942 | Musher | 424/195.1 |
| 2,382,242 | 8/1945 | Lindow et al. | 426/72 |
| 2,890,151 | 6/1959 | White | 514/61 |
| 3,278,383 | 10/1966 | White et al. | 424/61 |
| 3,522,350 | 7/1970 | Goldberg et al. | 424/195.1 |
| 3,530,217 | 9/1970 | White et al. | 514/57 |
| 3,628,971 | 12/1971 | Karchmar | 426/545 |
| 3,883,505 | 5/1976 | Hamuro | 534/845 |
| 3,948,801 | 4/1976 | Braddon et al. | 252/455 A |
| 4,011,206 | 3/1977 | Higginbotham | 530/370 |
| 4,075,406 | 2/1978 | Melaja et al. | 536/127 |
| 4,154,822 | 5/1979 | Polimeni et al. | 514/54 |
| 4,180,561 | 12/1979 | Vinson | 424/71 |
| 4,321,360 | 3/1982 | Blount | 536/1 |
| 4,352,746 | 10/1982 | Bracco et al. | 252/398 |
| 4,361,697 | 11/1982 | Dobberstein et al. | 536/128 |
| 4,380,506 | 4/1983 | Kimura et al. | 252/398 |
| 4,459,285 | 7/1984 | L'Oreal | 424/74 |
| 4,499,267 | 2/1985 | Scifoni | 44/51 |
| 4,511,559 | 4/1985 | Szendrei et al. | 514/54 |
| 4,525,306 | 6/1985 | Yajima | 260/428 |
| 4,536,496 | 8/1985 | Shimuzu et al. | 514/54 |

FOREIGN PATENT DOCUMENTS

| | | |
|---|---|---|
| 0201956 | 11/1986 | European Pat. Off. . |
| 1569849 | 1/1971 | Fed. Rep. of Germany . |
| 2209856 | 9/1973 | Fed. Rep. of Germany . |
| 3207005 | 9/1982 | Fed. Rep. of Germany . |
| 3130894 | 2/1983 | Fed. Rep. of Germany . |
| 1573315 | 7/1969 | France . |
| 2077708 | 11/1971 | France . |
| 2229388 | 12/1974 | France . |
| 2276830 | 1/1976 | France . |
| 2424024 | 11/1979 | France . |
| 2484836 | 12/1981 | France . |
| 856914 | 12/1960 | United Kingdom . |
| 2060378 | 5/1981 | United Kingdom . |
| 01713 | 3/1986 | World Int. Prop. O. . |

OTHER PUBLICATIONS

Article, "Measurement of and Protection from in Vivo Lipid Peroxidation", Al L. Tappel, pp. 1-47.
Article, "Estimation of Product of Lipid Peroxidation", . . . Placer et al, pp. 359-365.
Ames, Science 221:1256-64 (1983).
Chemical Abstracts, vol. 91, p. 495, Abstract No. 122353s (1979), "Fractionation of Antioxidative Constituents of 'Okara'", Y. Nakamura.
Patent Abstracts of Japan, C Field, vol. 4, No. 98, Jul. 15, 1980, The Patent Office Japanese Government, p. 134 C 18 (Kurorera).
Patent Abstr. of Japan, C Section, vol. 1, No. 27, Mar.

(List continued on next page.)

Primary Examiner—John W. Rollins
Attorney, Agent, or Firm—Ladas & Parry

[57] ABSTRACT

A food supplement which comprises in combination: (i) as an essential active antioxidant ingredient, a material characterized by stability for an extended period of time, at least in the dry state, under ambient conditions and which is selected from the group consisting of water soluble extracts prepared from plant tissue and fractions separable from such extracts by chromatography, and (ii) an orally ingestible diluent or carrier.

21 Claims, 11 Drawing Sheets

OTHER PUBLICATIONS 28, 1977, The Patent Office Japanese Gov., p. C 3969, Kokai-No. 51-142-514.

Patent Abstr. of Japan, C Section, vol. 1, No. 48, May 11, 1977, The Patent Office Japanese Govn., p. 6C77, Kokai-No. 52-3-845.

Patent Abstr. of Japan, C Field, vol. 8, No. 145, Jul. 6, 1984; The Patent Office Japanese Govn., p. 57C232, Kokai-No. 59-51,763.

A. Pinsky et al., "Lipoxygenase Content and Antioxidant Activity of Some Fruits and Vegetables", J. Food. Sci., vol. 36, pp. 571-2 (1971).

Patent Abstr. of Japan, C Field, vol. 7, No. 122, May 26, 1983; The Patent Office Japanese Govn., p. 136,C,168, Kokai No. 58-42,686.

Tadeusz Witas, "the Use of Plant Extracts as Antioxidants During Production of Fish Meal", Veterinary Medicine XXVIII, pp. 430-433.

CFTA Cosmetic Ingredient Dictionary, Third Ed., p. 298, Describes a Spinach Extract.

King, Amer. Dispensatory, 1870, pp. 548-551, 832 and 873.

Steinmetz, Codex Vegetabilis, 1957, pp. 57 and 59, 1156 and 1214.

Wren, Potter's Cyclopedia, 1950, pp. 108, 148 and 254.

Yen Tsai, et al., Planta Medica, pp. 460-461, 1985.

FOOD SUPPLEMENTS

FIELD OF THE INVENTION

The present invention relates to food supplements containing an antioxidant extracted from plants.

BACKGROUND OF THE INVENTION

It has been recognized for many years that the mammalian body requires for its nutrition relatively large amounts of fats, carbohydrates and proteins, and by contrast relatively small amounts of vitamins and minerals; lack of these latter classes of substances has been held to be accountable for the absence of general good health as well as the incidence of various specific bodily ailments. Vitamins and minerals are normally ingested or otherwise produced from the mammalian diet, but to a certain extent may also or alternatively be produced in the body. For various reasons which may be related to the source of supply or the manufacturing processes used, foods are sometimes lacking or deficient in vitamins and/or minerals, and even where vitamins are synthesized in the body, such a process may not produce the amount required. Over a period of time there has therefore grown up the use of food supplements, to supply the ingredients of this nature required by the body, but which are either no produced therein in sufficient amounts, or are not supplied thereto by the regular diet of the subject in sufficient amounts.

Food supplements are not at the present time, however, restricted merely to a content of vitamins and minerals, as the sole active ingredients. Other materials which are intermediate in metabolic processes and which it is thought may not be produced i sufficient amounts (at least in subjects with abnormal metabolism) may also be present in food supplements. Examples of such other materials are unsaturated fatty acids, such as linoleic acid, gamma-linolenic acid, dihomo-gamma-linolenic acid arachidonic and eicosapentaenoic acids, as well as physiologically compatible derivatives thereof, such as salts, esters and amides of such acids, which may be metabolized in the body to prostaglandins. Prostaglandins are an important group of local hormones which act within the body tissues in which they are synthesized, in roles which are not entirely understood, though they may act at least to lower blood pressure, and to induce smooth muscle to contract.

Horrobin, in Med. Hypotheses 6: 469-486 (1980), has also proposed that a metabolic abnormality in the synthesis of certain prostaglandins is responsible for allowing an initial cancer cell to divide indefinitely, the abnormality being in particular, inhibition of the enzyme delta-6-desaturase which converts essential unsaturated fatty acids in normal cells to prostaglandins. He has also proposed pharmaceutical compositions (see e.g. EP No. 0037175 published Oct. 7, 1981 and prior patent applications referred to therein, the contents of which are to be regarded as incorporated herein by reference) comprising certain unsaturated fatty acids together with other ingredients which enhance formation in the body of essential prostaglandins and therefore bypass the metabolic abnormality referred to above.

Vitamin E is known to protect red blood cells, vitamin A and unsaturated fatty acids from oxidation, and to possess an important function in muscle maintenance. The possible influence of vitamin E on fertility is not regarded as having been proved, at least so far as humans are concerned. Ames, in Science 221: 1256-64 (1983), has suggested that certain mutagens and carcinogens in the diet may act through the generation of oxygen radicals, which may also play a role in the initiation of degenerative processes possibly related to cancer, heart disease and aging, and that dietary intake of natural antioxidants (many of which are identified as anticarcinogenic) could be an important aspect of the body's defense mechanism against such agents. Ames brings references to show that vitamin E is the major radical trap in lipid membranes, has been used clinically in a variety of oxidation-related diseases, ameliorates both the cardiac damage and carcinogenicity of adriamycin and daunomycin, protects against radiation-induced DNA damage, and increases the endurance of rats during heavy exercise. It is of interest that carotenoids such as beta-carotene, as well as ascorbic acid (vitamin C), are also mentioned by Ames as examples of a small number of other substances having both antioxidant and anticarcinogenic activity.

The present inventors have discovered that certain substances extracted from plants, as will be described hereinbelow, have antioxidant properties believed to be superior to those of the synthetic antioxidants butylated hydroxy anisole (BHA) and butylated hydroxy toluene (BHT).

Moreover, the inventors have also discovered that not only are the antioxidant properties of these plant-extracted substances apparently superior to those of vitamin E, but that similarly to vitamin E they improve the synthesis in vivo of prostaglandins, and that furthermore, they have antiaging and anticancer properties.

Vitamin E capsules and other liquid and solid preparations are listed (e.g.) in the U.S.P., and proprietary preparations are also available. The Physicians' Desk Reference (1982), publ. Medical Economics Co. Inc., Oradell, N.J., U.S.A. lists some 34 proprietary multivitamin preparations containing vitamin E, For a description of human requirements and uses of vitamin E, reference may be made Martindale, The Extra Pharmacapoeia, e.g. 28th Edition (1982) at page 1663 et seq. It is of interest in relation to the foregoing discussion that it has been recommended that at least 0.4 mg. alphatocopherol be administered for each gram of polyunsaturated acids. The relevant contents of these various publications are to be regarded as incorporated herein by reference. It is believed that the experiments carried out by the present inventors and described herein show that it should be possible to advantageously replace vitamin E where currently used by the water-soluble antioxidant materials defined in the present invention.

It is accordingly an object of the present invention to produce antioxidant plant extracts which may be used in place of vitamin E in food supplements.

It is also an object of the invention to use such antioxidant plant extracts in food supplements either alone or together with one or more vitamins and/or minerals and/or unsaturated fatty acids.

It is a further object of the invention to use such antioxidant plant extracts together with one or more unsaturated fatty acids known to be intermediates in the metabolic formation of prostaglandins in the mammalian body, with or without other ingredients which are known to enhance formation in the body of essential prostaglandins.

Other objects of the invention will appear from the description of the invention which follows.

The stable, water soluble plant-extracted antioxidants which constitute an essential ingredient of the present food supplements, and certain uses of these antioxidants, are described and claimed in U.S. Pat. Application Ser. No. 846,599, filed Mar. 31, 1986, now U.S. Pat. No. 4,857,325 (a continuation-in-part from Application Ser. No. 726,540, filed Apr. 24, 1985 as well as in European Patent Application No. 201,956 published November 1986.

SUMMARY OF THE INVENTION

The present invention thus provides a food supplement which comprises in combination: (i) as an essential active antioxidant ingredient, a material characterized by stability for an extended period of time, at least in the dry state, under ambient conditions and which is selected from the group consisting of water soluble extracts prepared from plant tissue and fractions separable from such extracts by chromatography, and (ii) an orally ingestible diluent or carrier.

The plant tissue may be constituted by e.g. fresh leaves or stems.

In a particular embodiment, the plant tissue may be prepared from plants of the group consisting of Spinacia (e.g. *Spinacia oleracea:* spinach), Trifolium (e.g. clover), Medicago (e.g. *Medicago sativa:* alfalfa), Zea (e.g. *Zea mays:* corn), Nicotiana (e.g. *Nicotiana tabacum:* tobacco), Pennisetum, Algae and Allium (e.g. onion and garlic).

In an alternative particular embodiment, the plant tissue may be prepared from plants of the order Chenopodiales (as defined herein). For the purposes of the present invention, this order comprises the plant families Aizoaceae, Amaranthaceae, Caryophyllaceae, Chenopodiaceae (as defined herein), Nyctaginaceae, Phytolaccaeae and Portulacaceae. Presently preferred families are Aizoaceae and Chenopodiaceae (as defined herein). Chenopodiaceae is for the purposes of the present patent application defined as the plant family by that name known to one skilled in the botanical art, with the exception of Spinacia, Examples of the family Chenopodiaceae within the scope of this definition are Atriplex, e.g. "Mountain Spinach" (*Atriplex hortensis*), otherwise known as "Orach", and Beta, e.g. the beet varieties included within *Beta vulgaris.* Aizoaceae is for the purposes of the present patent application defined as the plant family by that name known to one skilled in the botanical art, an example being Tetragonia, e.g. "New Zealand Spinach" (*Tetragonia expansa*).

Where, in the description which follows, reference is made to "spinach", it will be appreciated that a member of the botanical group Spinacia, and in particular *Spinacea oleracea,* is specifically intended. However, when the antioxidant extractive process particularly described herein in relation to "spinach", is applied to other plants of the group consisting of Spinacia, Trifolium, Medicago, Zea, Nicotiana, Pennisetum, Algae and Allium, or to members of the plant order Chenopodiales (as defined herein), preferably members of the plant families Chenopodiaceae (as defined herein) and Aizoaceae, the same fractions are obtained having the same properties, as when the extractive process for *Spinacea oleracea* is used. Without limiting the scope of the invention in any way, it may be noted that "New Zealand Spinach" (*Tetragonia expansa*) in particular, may be substituted for the spinach (*Spinacia oleracea*) in the detailed description herein, including the description of the preferred embodiments which follows, with comparable results.

DETAILED DESCRIPTION OF THE INVENTION

Figure 1:
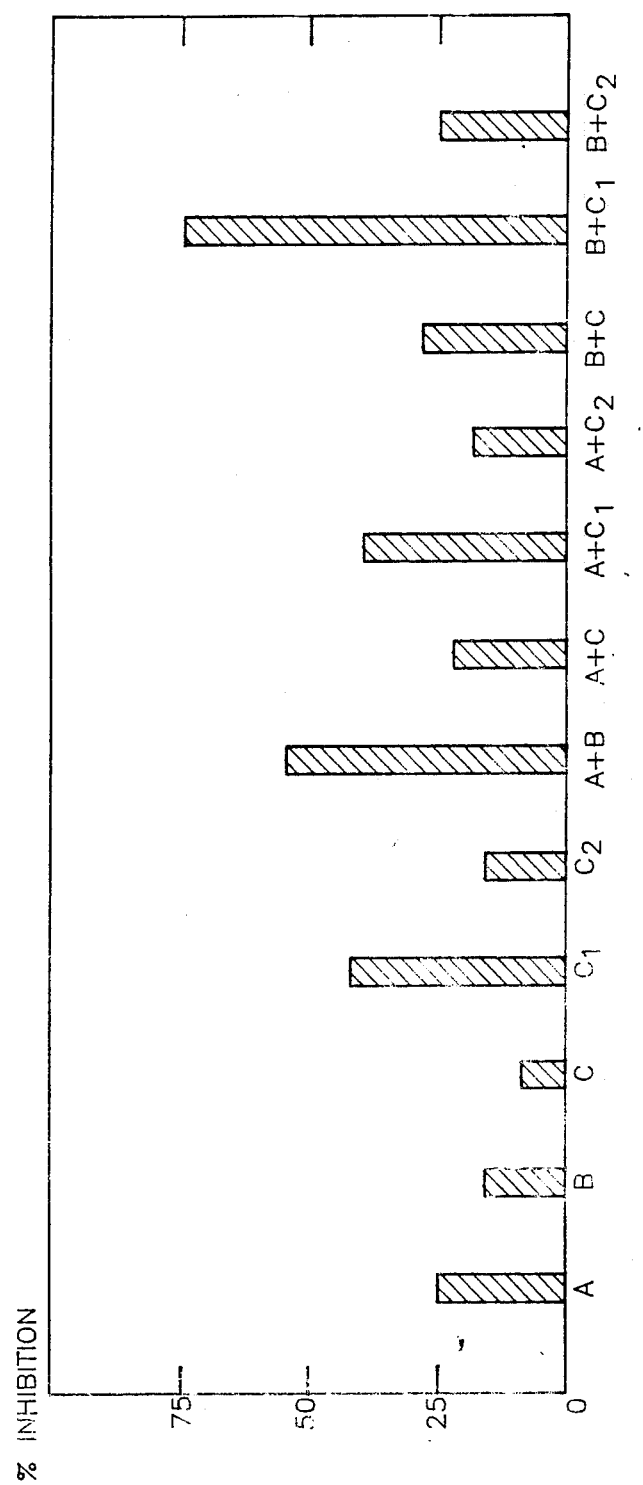
FIG. 1 is a chart which shows antioxidative synergism of selected antioxidant fractions.

The present invention provides food supplements which comprise plant-extracted water-soluble antioxidant materials. Suitable plants for extraction have been specified above, but other plants may be utilized, provided that extraction of their tissue, in particular fresh leaves and/or stems, provides a water-soluble and stable antioxidant. It will be appreciated that the presence of the antioxidants in the food supplements may serve not only to introduce the inherent beneficial antioxidative effect into the mammalian body, but also to preserve from deterioration other substances which may be present in the food supplements themselves.

The antioxidant effect of the water-soluble extracts may be determined for example by the thiobarbituric acid (TBA) test. This test is described in Food Res. 23: 620 (1958). It is believed that reduction of the peroxide level of the skin may provide a useful indication of the antioxidative action of the present materials in relation to body tissues generally, when these materials are ingested in the form of the food supplements of the present invention. Accordingly, the level of peroxide in the skin may be determined by assay of a sample of untreated skin which is peeled from a test animal. A pre-weighed sample from 10 to 50 mg. is homogenized in 0.2M phosphate buffer pH 6.5 and centrifuged. The supernatant is collected and the peroxide level is determined using the TBA test. A sample of skin from the same animal which has been treated with the antioxidant material which is an essential component of the food supplement according to the invention is also peeled and the peroxide level is determined. A reduction in the peroxide level of about 35%, when the present antioxidant is applied as 0.5% w/w dispersion in a petrolatum base, is the criterion for determining if a given plant extract is a useful antioxidant.

Further experiments described infra show that the presently used antioxidants are (i) comparable with vitamin E in improving the synthesis of prostaglandins in vivo. (ii) comparable with vitamin E in inhibiting lipid peroxidation in tissue culture, and (iii) superior to vitamin E in reducing the peroxide level of the skin. It is believed to be a reasonable conclusion, as a result of the experimental work described herein, looked at as a whole, that the antioxidants which form an essential ingredient of the food supplements of the present invention are at least as active physiologically as vitamin E, if not more active in certain respects, and may therefore be substituted for vitamin E in existing food supplements.

The water-soluble antioxidant may be extracted from the plant material using a plant to water ratio in the range of 0.5:100 to 1.0:0.5 (w/v), preferably 2:1 (w/v), after comminution of the plant material. The comminution may be carried out at temperatures within the range of about 4° to about 100° C., preferably at about 25° C., using a blender, grinding apparatus or any other type of apparatus which will cause fragmentation of the cell walls. The extracted plant material is separated using filtration, centrifugation, decantation, froth flotation, or any other conventional method used for separating a solid from a liquid.

The crude antioxidant may be used as obtained from the plant, either in dilute form or as an aqueous mixture or as a purified extract. Generally it is preferred to separate the aqueous extracting medium from the dissolved antioxidant by evaporation or lyophilization of the liquid portion to provide a dry, water soluble antioxidant. The crude extract may be purified using chromatographic techniques.

Generally, the powder is dissolved in water to form a 10 to 30% w/w solution which is applied to the top of the column and is allowed to move through the column. The various fractions are eluted using water as washing medium and the various fractions are separately collected. The individual fractions may be further purified by a second chromatographic procedure using a packing medium having a smaller pore size than in the preceding step.

Sephadex G-25 may be utilized as a chromatographic column separation medium to resolve the crude extract from spinach into a brown fraction, a yellow fraction and an orange fraction. The orange fraction may be extracted with water and further separated chromatographically using a Sephadex G-10 column. Sephadex G-25. medium grade, is dextran that has been cross-linked with epichlorohydrin and has a pore size of 50–150 $\mu$m. Sephadex G-10 is dextran that has been cross-linked with epichlorohydrin and has a pore size of 40–120 $\mu$m. Thin layer chromatography is utilized to separate a yellow fraction from the orange fraction. The Sephadex materials are described in Gel Filtration Theory and Practice, Pharmacia pp. 1–64. which is incorporated by reference.

The inventors have isolated several different active antioxidant fractions, which may be used separately or in combination. Several of the combined fractions have been shown to have higher activity than the crude fraction. The relative amounts of the brown, orange and yellow fractions may be varied to give optimum results. Generally, any two fractions may be used at weight ratios of 1:99 to 99:1, based on the total weight of the combined fractions. However, it is also within the scope of the invention to combine together more than two fractions.

Both crude and purified antioxidants in accordance with the invention are stable to high temperature, e.g. at the temperature of boiling water for 30 minutes. Moreover, they have good stability for extended periods under ambient conditions. By way of example, the crude extract from spinach in powder form has been kept for more than one year at room temperature, without any loss in its antioxidant activity.

Toxicity studies have been carried out using both crude and purified fractions, and no pathological changes have been detected when the materials have been administered by injection or orally.

The antioxidants have also been shown to be effective in inhibiting tumors such as fibrosarcoma induced by methylcholanthrene and skin cancer such as squama cell carcinoma which is induced by dimethylbenzoicanthrene and 4B-phorbol 12-myristate-13-acetate, and ultraviolet light. This finding lends support to the postulation in the Ames article (above), of a relationship between antioxidant activity and anticancer activity.

The present invention includes food supplements wherein the plant extracts are chromatographically separable on dextran which has been cross-linked with epichlorohydrin and has a pore size of 50–150 $\mu$m, into fractions which are colored brown(A). yellow(B) and orange(C), and of which fraction A is chromatographically purifiable on a substance which is either (i) a condensation product of cellulose with epichlorohydrin and triethanolamine having a capacity of 0.3 to 0.4 meq./g. and a particle size 0.05–0.2 mm., or (ii) dextran which has been cross-linked with epichlorohydrin and has a pore size of 40–120 $\mu$m. to give a fraction ($A_1$) having an infrared spectrum with substantially the following features, namely, broad band at 3300–3400 cm.$^{-1}$, strong band at 1650 cm.$^{-1}$, additional bands at 1730, 1540, 1250 and 1080 cm.$^{31\ 1}$, weak bands at 2920, 1400 and 1150 cm.$^{-1}$, and of which fractions, fraction C is chromatographically separable on dextran which has been cross-linked with epichlorohydrin and has a pore size of 40–120 $\mu$m, into fractions colored dark brown($C_1$) and yellow orange($C_2$).

The present invention further includes food supplements in which the antioxidant material comprises at least one substance, and preferably a combination of two substances, selected from fractions A, $A_1$, B, $C_1$ and $C_2$, as described herein. Moreover, the antioxidant materials used as an essential ingredient of the present food supplements may be any materials having substantially the infrared spectra described herein.

In the food supplement according to the invention, the antioxidant material may be prepared by a process which comprises the step of extracting plant tissue with water. The plant tissue may be comminuted prior to or simultaneously with the extraction step. The extraction and/or comminution is preferably carried out at temperatures within the range of about 4° C. to about 100° C., e.g. at about 25° C. Since the antioxidant materials are in general sufficiently stable, not to be adversely affected by boiling with water, in an alternative embodiment the plant material may be extracted by boiling with water, and comminution is not essential. It is preferred that the product of the extraction step is resolved by chromatography into fractions.

The food supplement according to the invention includes as an essential component an orally ingestible diluent or carrier; this may for example comprise a substance selected from a manufactured cereal, fruit or vegetable product, a beverage or beverage concentrate, or any inert diluent, carrier or excipient known in the pharmaceutical art. It is intended generally that the antioxidant material may be used in food supplements, in any of the forms in which these are known and practised in the art.

Thus, the feed supplements may take the form of, e.g., breakfast cereals, fruit or vegetable purees or beverages, other beverages or beverage concentrates generally (including those in the form of e.g. powders, granules, flakes or crystals, which are intended to be mixed with hot or cold water and/or milk). The food supplements may also generally be in the form of powders, tablets, capsules, solutions, concentrates, syrups, suspensions or dispersions. It will be evident that when the food supplements take the form of dispersions or suspensions, it will usually be necessary to use an acceptable (i.e. non-toxic and otherwise suitable) dispersing or suspending agent, as is well known in the food supplement and pharmaceutical arts.

It will be appreciated that the stability of the antioxidants used in the present invention enables them to act in one and the same composition in a dual capacity, namely, in the first place to inhibit oxidation in diluents which are liable to oxidation, such as in ground meat products or their vegetable (e.g. soya) analogues, or in peeled potato products such as chips or crisps, and in the second place to act as the desired in vivo antioxidant in the body. The ability of the antioxidant materials to inhibit oxidation in oxidation-prone foodstuff diluents will be demonstrated hereinafter. It is well within the competence of one skilled in the art to determine the amount of the water-soluble antioxidant to be added to an oxidation-prone foodstuff, merely to inhibit oxidation thereof for a given period of time e.g. for the storage and/or shelf-life of the foodstuff (which mere inhibition of oxidation does not fall within the scope of the present invention), or on the other hand to determine the amount of the water-soluble antioxidant to be added to such an oxidation-prone foodstuff, which will not only inhibit oxidation thereof for a given period of time, but will additionally be present in an amount sufficient so that it will act as an effective in vivo biological antioxidant, in accordance with the present invention.

The present invention also provides compositions suitable for administration by injection, for the purpose of providing an in vivo biological antioxidant effect, which comprise a water-soluble antioxidant as described herein, together with a suitable diluent or carrier.

The present invention moreover includes the food supplements described herein, which are adapted for administration to non-human mammals.

The antioxidant material may be present in the food supplement in any suitable proportion which will be related inter alia to the antioxidant activity of the particular material utilized. In general, the antioxidant material may constitute e.g. about 0.001 to about 1.0 %, and preferably about 0.005 to about 0.1 % by weight of the food supplement.

It will be appreciated that the water-solubility of the plant-extracted antioxidants used in the present food supplements presents a contrast to the water-insolubility of vitamin E. It is believed that this water-solubility is a distinct advantage, because it enables the food supplements to be in the form of readily prepared and administered aqueous solutions in which the diluent comprises water.

The present invention further includes food supplements which also include any of the known vitamins. Thus for example, the present food supplements (which may be, but need not be, in the form of aqueous solutions) may comprise at least one water-soluble vitamin selected from thiamine, riboflavin, niacin, pyridoxine, pantothenic acid, biotin, folic acid, cobalamin and ascorbic acid. Alternatively or additionally, the present food supplements may comprise at least one oil-soluble vitamin selected from retinol, calciferol, tocopherol and menadione. The food supplements of the present invention may also comprise in combined form at least one element selected from sodium, potassium, calcium, phosphorus, magnesium, chlorine and sulfur, and additionally or alternatively, at least one element selected from iron, copper, iodine, manganese, cobalt, zinc, molybdenum, fluorine, selenium and chromium.

The food supplements of the present invention may also comprise (regardless of whatever other optional ingredients may or may not be present), unsaturated fatty acids, known to be metabolized in the body to prostaglandins, as for example, linoleic acid, gamma-linolenic acid, dihomo-gamma-linolenic acid arachidonic and eicosapentaenoic acids, as well as physiologically compatible derivatives thereof, such as salts, esters and amides of such acids.

Aqueous extraction of the antioxidants

Leaves from Spinacia oleracea were homogenized with $H_2O$ at 25° C. at a ratio of 2:1 (w/v) in a Waring Blender for 5 minutes. The resulting homogenate was filtered through cheesecloth and then centrifuged at $15000 \times g$ for 10 minutes. The supernatant was collected and lyophilized.

The isolation and purification of antioxidant fractions from the crude homogenate preparation was achieved through gel filtration followed by preparative TLC or HPLC. 1 g. of the lyophilized powder of the crude homogenate was dissolved in 5 ml. $H_2O$ and after centrifugation at $20000 \times g$ for 10 minutes, the supernatant was applied to a Sephadex G-25 column (40 cm. $\times$ 2.5 cm.), equilibrated and eluted with water. Fractions of 5 ml. were collected and each was assayed for antioxidant activity. The active fractions (A, B and C) were pooled (fraction A has a brown, B a yellow and C an orange color), and lyophilized. Fraction C was further purified. The lyophilized material of fraction C was dissolved in water to form a 20% solution (w/v), centrifuged at $20000 \times g$ for 10 minutes, and the supernatant was chromatographed on a Sephadex G-10 column (40 cm. $\times$ 2.5 cm.), and equilibrated with water. Fractions $C_1$ and $C_2$ were collected separately and lyophilized as before. Lyophilized fraction $C_1$ was dissolved in a minimum amount of water, applied to 0.2 mm. silica gel plates (DC-Karten SIF, Riedel-Dollaen AG., sleeze-Hanover) and developed in 30:60 v/v $H_2O$-ethanol. The active fraction was identified by its weak (pale) yellow color and was extracted from the silica gel plate with water and lyophilized.

Figure 7:
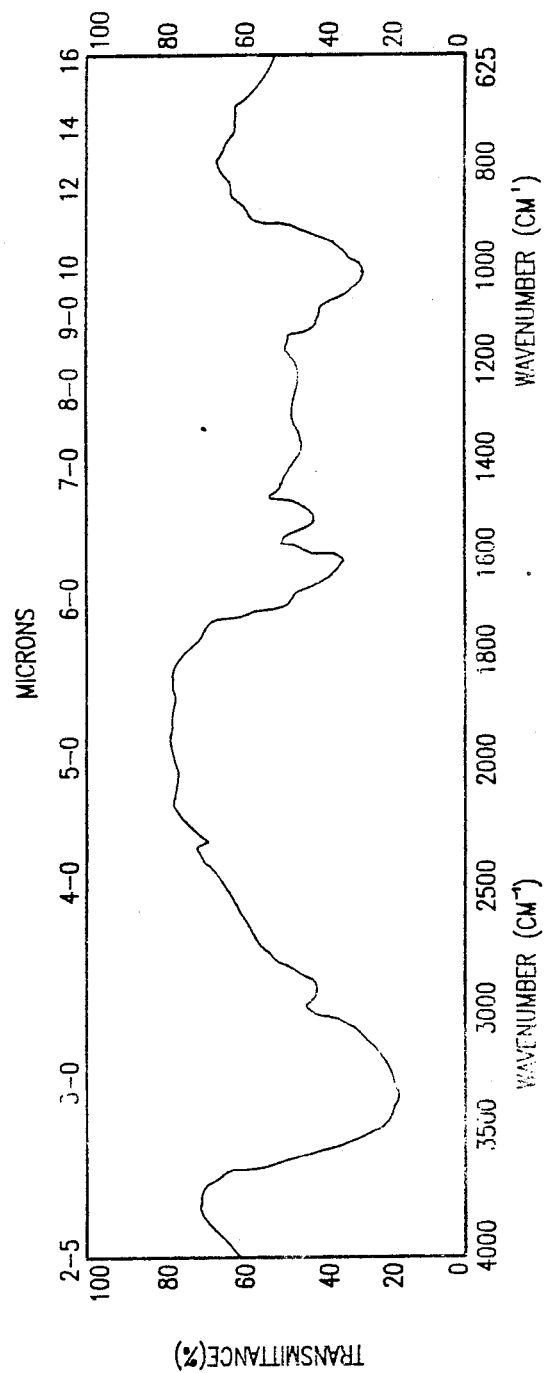
FIG. 7 shows an infrared curve of the present antioxidant material, fraction $A_1$, isolated from spinach.

A further purification was carried out using DEAE cellulose (small size). The fraction identified hereinabove as A was dissolved in water and passed through a 5 cm. $\times$ 1 cm. column packed with DEAE cellulose (small size). (Alternatively, the column packing may be Ecteola, a condensation product of cellulose with epichlorohydrin and triethanolamine having a capacity of 0.3 to 0.4 meq./g. and a particle size 0.05–0.2 mm.) The column was equilibrated with water that was acidified to a pH of 5–6 with 0.2N HCl. The column was eluted with a solution of HCL, pH 2.0 and the eluted material was recovered as a powder by vacuum evaporation. A pure product ($A_1$) was obtained which had the infrared curve of FIG. 7. The powder was further purified by dissolving in water at a concentration of 20 ug./ml. and passing through a high pressure liquid chromatography silica 60 column (250 mm.×4 mm.), with a 90:10 solution of water:acetonitrile applied at a rate of 0.5 ml./min. A fraction was obtained which had a retention fraction at 5.4 nanometers (UV absorption).

The preparation and activity of the essential active ingredients of the food supplements according to the present invention will be illustrated in the following Examples.

EXAMPLE 1

From the crude extract of the plant material, 3 antioxidant active fractions (A, B and C) were obtained following the first step of purification. Fraction C was further purified on a column packed with Sephadex G-10 and two other active fractions were obtained by elution with water ($C_1$—dark brown and $C_2$—yellow orange). Fraction $C_1$ was finally purified using HPLC. In studying the antioxidant activity of the crude plant extracts and the isolated fractions, both the inhibition of linoleate oxidation by lipoxygenase and the inhibition of autooxidation of peroxides were used as criteria for antioxidant activity.

The antioxidant fractions exhibited synergistic activity. The synergism obtained with the natural isolated antioxidants is shown in FIG. 1, which depicts the percentage inhibition on lipid oxidation of 1 mg. each of single purified antioxidant fractions, as well as the analogous percentage inhibition using combinations of 0.5 mg. each of two such fractions. By way of example, it may be seen that this synergism increased the potency produced by the compounds from 167% ($B+C_2$) up to 250% ($A+B$), without increasing the total antioxidant content.

Since lipid peroxidation catalyzed by hemeproteins is a basic deteriorative and pathological reaction, the effectiveness of the isolated fractions to prevent such peroxidation was followed. It was found that the isolated fractions prevent such peroxidation induced by hemoglobin, cytochrome C and myoglobin, in a similar way to the inhibition of lipoxygenase-induced oxidation.

The purified antioxidant fractions retained their antioxidative activities for months, without any loss, when kept at room temperature. Moreover, boiling the purified antioxidants for up to 30 minutes, did not reduce their antioxidant capacity.

Figure 3:
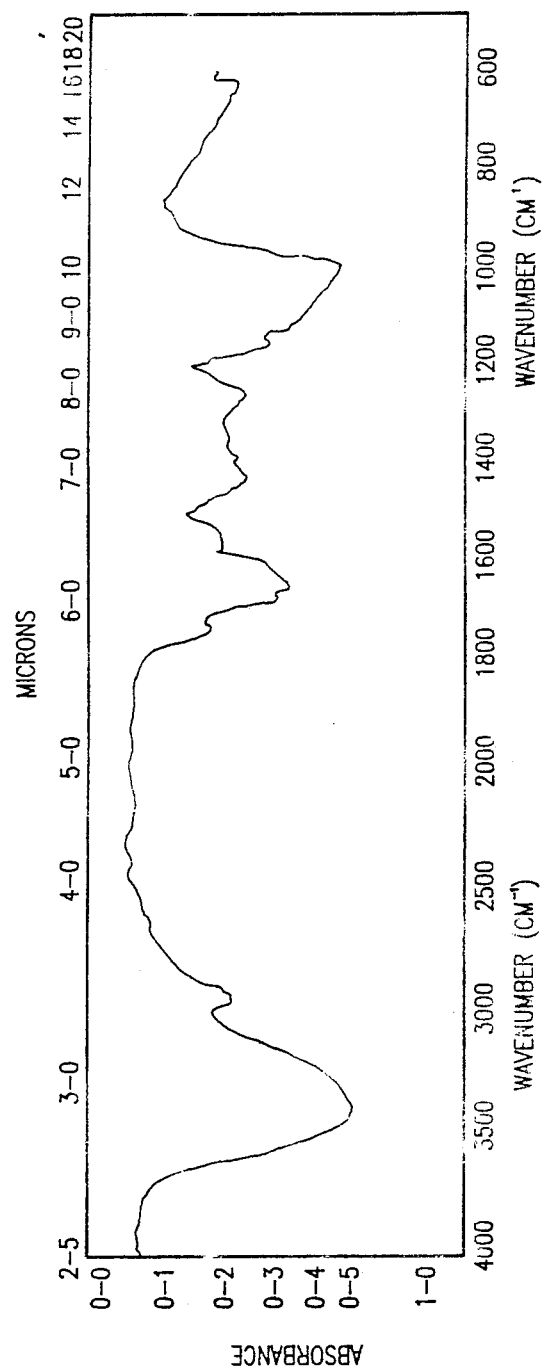
FIG. 3 shows an infrared curve of the present antioxidant material, fraction A, isolated from spinach.

The following infrared data was obtained from the spinach-derived fractions:

A: (see FIG. 3) broad band at 3400 cm.$^{-1}$, strong bands at 1050 and 1650 cm.$^{-1}$, weak bands at 1250 and 1430 cm.$^{-1}$.

Figure 4:
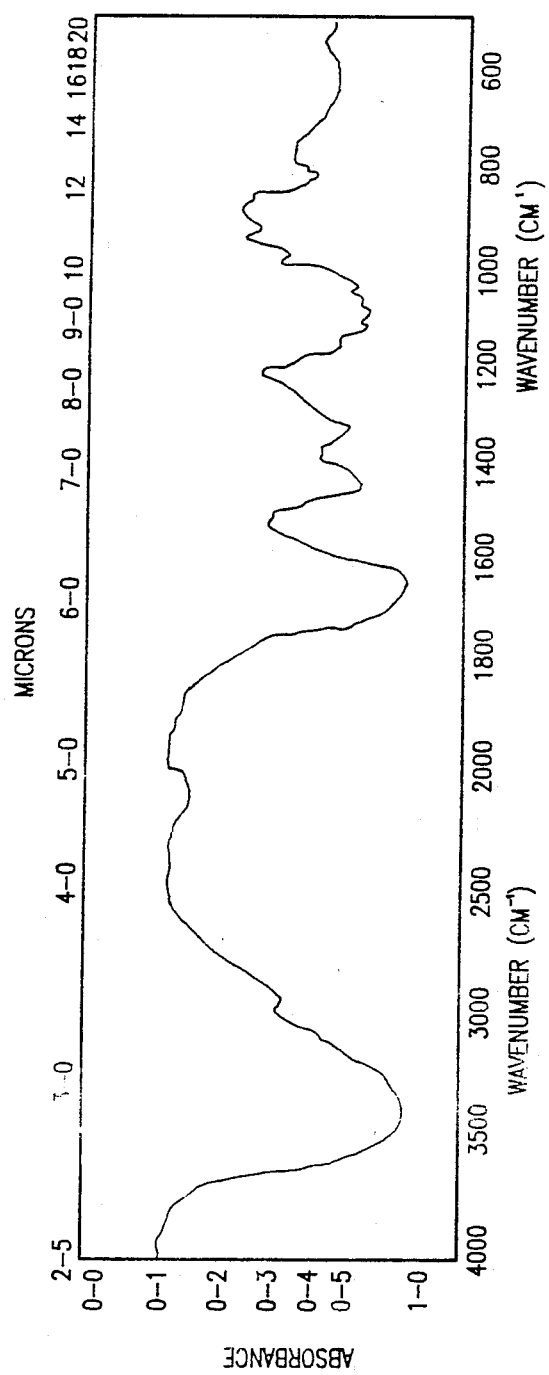
FIG. 4 shows an infrared curve of the present antioxidant material, fraction B, isolated from spinach.

B: (see FIG. 4) broad bands at 3400, 1640 and 1080 cm.$^{-1}$, additional bands at 1420, 1300 and 810 cm.$^{-1}$.

Figure 5:
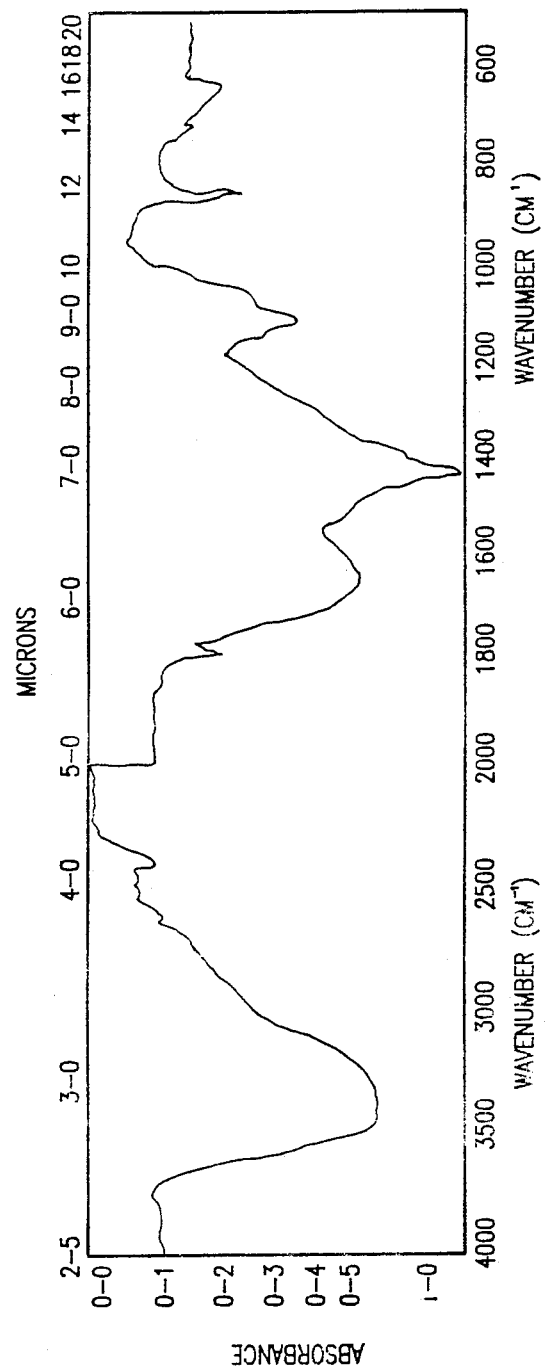
FIG. 5 shows an infrared curve of the present antioxidant material, fraction C, isolated from spinach.

C: (see FIG. 5) broad bands at 3400 and 1600 cm.$^{-1}$, strong band at 1390 cm, additional bands at 1070 and 820 cm.$^{-1}$.

Figure 6:
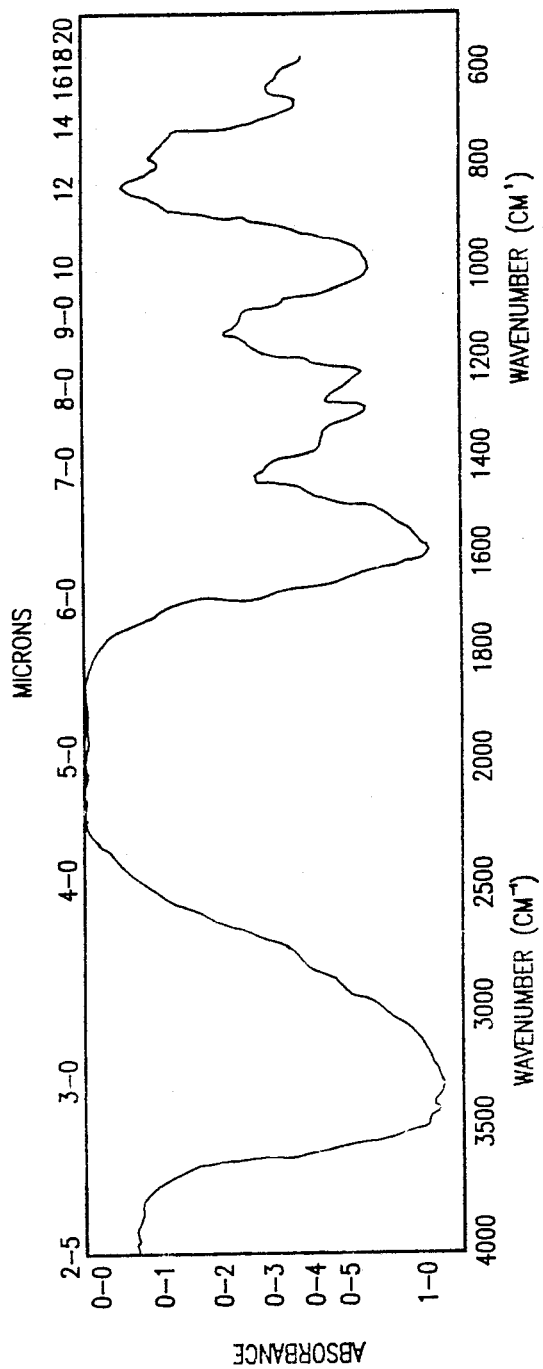
FIG. 6 shows an infrared curve of the present antioxidant material, fraction $C_1$, isolated from spinach.

$C_1$: (see FIG. 6) broad band at 3300 cm.$^{-1}$, strong band at 1620 cm.$^{-1}$, additional bands at 1390, 1320, 1080 and 770 cm.$^{-1}$.

$A_1$: (see FIG. 7) broad band at 3300-3400 cm.$^{-1}$, strong band at 1650 cm.$^{-1}$, additional bands at 1730, 1540, 1250 and 1080 cm$^{-1}$, weak bands at 2920, 1400 and 1150 cm.$^{-1}$.

EXAMPLE 2

Samples of lotions and appropriate controls were applied to mice or rat skin for a fixed period. The application was done once a day. Experiments were terminated by killing the animal, peeling the skin and freezing it in liquid nitrogen. Samples of the frozen skin were homogenized in 0.2M phosphate buffer, pH 6.5. After centrifugation, the supernatant was collected and analyzed for the peroxide value using the TBA (thiobarbituric acid) test as described by Sinnhuber et al, Food Res. 23:620 (1958).

In the experiments which follow, newborn (hairless) rats were used. It is generally considered that the penetration through the skin of newborn rats is better than in adult rats, since at this stage they have not yet developed any fur.

Test No. 1

In this experiment the control group was treated with Vaseline only, while the test group was treated with Vaseline containing a $C_1$ fraction. The test was run for 12 days and the results are presented in Table 1.

TABLE 1

| GROUP | TBA (O.D. 532/1 g. tissue) | Level of Peroxidation | P value* (n = 3) |
|---|---|---|---|
| Control | 0.295 | 100% | 0.002 |
| +0.5% $C_1$ | 0.188 | 64% | 0.002 |

*standard deviation

It is clearly demonstrated that the $C_1$ penetrates the skin of newborn rats and consequently reduces the level of peroxides in the skin. Since peroxides, and the free radicals involved in their formation and breakdown, constitute one of the main routes leading towards aging, the activity of this unique antioxidant can be considered as an anti-aging factor.

Test No. 2

In this experiment the antioxidant was dissolved in Oil of Olay (a proprietary skin lotion) obtained in Israel (excellent solubility) and experiments similar to that described in No. 1 were performed. The results are presented in Table 2.

TABLE 2

| GROUP | TBA (O.D. 532/1 g. tissue) | Level of Peroxidation | P value* (n = 4) |
|---|---|---|---|
| Control (no treatment) | 0.295 | 100% | 0.002 |
| Control (Oil of Olay) | 0.230 | 78% | 0.005 |
| +0.15% $C_1$ | 0.200 | 68% | 0.011 |
| +1.5% $C_1$ | 0.191 | 65% | 0.010 |

*standard deviation

As in test no. 1, the antioxidant significantly reduced the level of peroxides in the skin. It is interesting to point out that in newborn rats, Oil of Olay without the antioxidant also reduced the peroxide level. This may be attributed to the commercial antioxidants present in the Oil of Olay which was used. It is possible that in newborn skin, due to its relatively high permeability, small amounts of these antioxidants can also penetrate the skin. However, in adult mice or rats, as will be shown later, Oil of Olay did not reduce the level of peroxides in the skin. On the contrary, in general, a small increase in peroxide level was detected, which perhaps may be attributed to traces of metals in the lotion.

EXAMPLE 3

In these experiments adult mice (2 months old) were treated as described in Example 2. The grown mice were shaved before applying the lotions to the skin. In this experiment the antioxidant was dissolved in Oil of Olay. Mice were sacrificed after 21 days. The results are presented in Table 3.

TABLE 3

| GROUP | TBA (O.D. 532/1 g. tissue) | Level of Peroxidation | P value* (n = 3) |
|---|---|---|---|
| Control (no treatment) | 0.338 | 100% | 0.019 |
| Control (Oil of Olay) | 0.400 | 118% | 0.026 |
| +0.3% $C_1$ | 0.240 | 71% | 0.002 |

*standard deviation

It seems that in grown mice the Oil of Olay slightly increases the level of peroxides while addition of the antioxidant at a concentration of 0.3% significantly reduced these peroxides, thus indicating that even with grown mice the antioxidant penetrates the skin.

When, in similar experiments, we tried the effect of 0.1% BHT, BHA and alpha tocopherol dissolved in Oil of Olay on the level of peroxides in the skin, no reduction of the level of peroxides was observed. These experiments suggest inter alia that the antioxidant activity of the present water-soluble materials is superior to that of alpha tocopherol and the other known antioxidants.

EXAMPLE 4

A new model for studying aging was developed. The new model involved the exposure of adult shaved mice to a UV lamp (sun lamp 300W) for a short period. As a result, the aging processes as expressed by the level of peroxidation were stimulated and the effect of the natural antioxidant was studied. Using this new technique, the optimal antioxidant dose for the inhibition of aging was determined.

In this experiment, a crude preparation of antioxidant (and not separated into its components as described elsewhere herein) was used.

Adult mice were shaved and the individuals were exposed to the UV light (Philips HP 3115), with or without antioxidant, for a short period of one minute for two days (two exposures in total). On the third day they were sacrificed and the level of peroxidation in the skin was determined by the TBA (thiobarbituric acid) test.

Controls without exposure to the UV light were also included. Antioxidant was dissolved in Oil of Olay. The results are presented in Table 4.

TABLE 4

Effect of antioxidant dose on aging (7 individuals in each group)

| GROUP | TBA (O.D. 532/1 g. tissue) | Level of Peroxidation | P value* (n = 7) |
|---|---|---|---|
| 1. no radiation | 0.147 | 16.7% | 0.010 |
| 2. radiation + Oil of Olay | 0.880 | 100% | 0.027 |
| 3. radiation + 0.3% antioxidant in Oil of Olay | 0.740 | 84% | 0.006 |
| 4. radiation + 0.4% antioxidant in Oil of Olay | 0.680 | 77% | 0.020 |
| 5. radiation + 0.5% antioxidant | 0.680 | 77% | 0.0 |

TABLE 4-continued

Effect of antioxidant dose on aging (7 individuals in each group)

| GROUP | TBA (O.D. 532/1 g. tissue) | Level of Peroxidation | P value* (n = 7) |
|---|---|---|---|
| in Oil of Olay | | | |
| 6. radiation + 1.0% antioxidant in Oil of Olay | 0.700 | 79% | 0.006 |

*standard deviation

The optimal dose of crude antioxidant is 0.3–0.4%.

EXAMPLE 5

Samples of human skin were obtained from a Plastic Surgery Department of a hospital. These samples were placed in a saline solution immediately after their removal from the patients.

The skin samples were exposed to UV rays (Philips Sun Lamps) for 5 minute intervals, three successive times with a 5 minute rest period between each exposure. The distance between the lamp and the tissue was 12 cm. The skin samples were stored for 3 days at 4° C., after which time they were peeled and homogenized. 20–30 mg. of peeled tissue were assayed for peroxide level using the spectrophotometric TBA test.

The results clearly demonstrate that the peroxide level of the skin tissue was raised due to the exposure to UV rays. Skin treated with the present water-soluble antioxidant and exposed to UV rays for the same period of time showed a peroxide level similar to the untreated control. These results are shown in Table 5.

TABLE 5

| Sample | TBA (O.D. 532/0.1 g. tissue) | Level of Peroxidation |
|---|---|---|
| Unexposed | 0.050 | 62.5% |
| Exposed | 0.080 | 100% |
| Exposed + Oil of Olay | 0.100 | 125% |
| Exposed + (A + B + C) + Oil of Olay | 0.050 | 62.5% |

The experiments run on human skin indicate the following:
(a) the antioxidant penetrates the skin;
(b) the antioxidant significantly reduces the level of peroxides.

It is noted that when a mixture of fractions A+B+C was used, an effective antioxidant result was observed.

EXAMPLE 6

The crude extract was tested in vivo for its effect on the immune response system in experimental mice. In these experiments, male Balb-C mice were injected intraperitoneally with 1 mg. of the crude extract from Spinacia oleracea per 0.2 ml. of phosphate buffer solution (PBS) per animal. Animals were sacrificed one, three and seven days after injection, following which their spleens were removed. Spleen cells ($10^7$ cells/ml. enriched RPMI) were cultured for 24 hours in the presence of CON A (concavalin-A) 2 ug./ml. and the supernatants thus obtained were tested for both IL-2 (interleukin-2) and CSF (colony stimulating factor). No significant differences were found between controls (i.e. animals receiving no treatment) and experimental animals, in their ability to produce IL-2 as well as CSF, indicating that the antioxidant has no adverse effect on the immune system. In addition, no pathological findings were observed in injected animals.

Additional testing determined that a single dose of 25 mg./mouse i.p. may be tolerated and that the $LD_{50}$ is in the range of 1400 mg./kg. for mice.

EXAMPLE 7

The $C_1$ fraction was dissolved in PBS (50 mg./10 ml.) and 0.2 ml. of this solution was injected i.p. into each mouse twice weekly. The $C_1$ fraction was also administered orally in an aqueous solution (1 mg./ml.) and the mice were allowed to drink the solution from a calibrated bottle to enable measurement of the quantity of the $C_1$ fraction consumed by each individual mouse to be determined. Each mouse was subsequently injected with 0.6 mg. methylcholanthrene, a known inducer of fibrosarcoma. Test series A and B were carried out as follows, in which the figures refer to the number of animals in which the appearance of tumors occurred/the number of animals in the group. Results are shown in Table 6.

TABLE 6

| Weeks after inoculation with methylcholanthrene | Controls | Groups treated with C1 antioxidant | |
|---|---|---|---|
| | | orally | i.p. |
| (TEST A) | | | |
| 5 | 4/20 | 1/10 | 1/10 |
| 6 | 9/20 | 1/10 | 1/10 |
| 7 | 14/20 | 3/10 | 2/10 |
| 8 | 16/20 | 3/10 | 2/10 |
| 9 | 18/20 | 4/10 | 2/10 |
| (TEST B) | | | |
| 7 | 1/10 | 0/8 | 0/9 |
| 8 | 3/10 | 0/8 | 0/9 |
| 9 | 4/10 | 0/8 | 0/9 |
| 10 | 4/10 | 0/8 | 0/9 |
| 11 | 6/10 | 1/8 | 0/9 |
| 12 | 7/10 | 1/8 | 0/9 |
| 13 | 7/10 | 2/8 | 1/9 |

At week 13 (test B), after as many as 25-29 injections, one mouse from each group was sacrificed and observed for gross internal changes (i.e. lymph nodes, spleen, liver, kidney, heart and lung, etc.); no significant changes and no pathological damage were observed. This demonstrated that even a prolonged treatment with the $C_1$ fraction by different routes of administration did not cause any damage to the treated mice. It was similarly observed that a 14-week treatment with crude antioxidant as used in the present invention caused no damage in the treated mice.

The in vivo experiments demonstrated that i.p. or oral administration with $C_1$ is effective in delaying the appearance and reducing the frequency of methylcholanthrene-induced tumors.

EXAMPLE 8

Skin tests on human volunteers using a 0.3% w/w dispersion of the crude extract in Oil of Olay have resulted in subjective improvement in the texture of the skin with no adverse effects in any test subjects.

EXAMPLE 9

Figure 2:
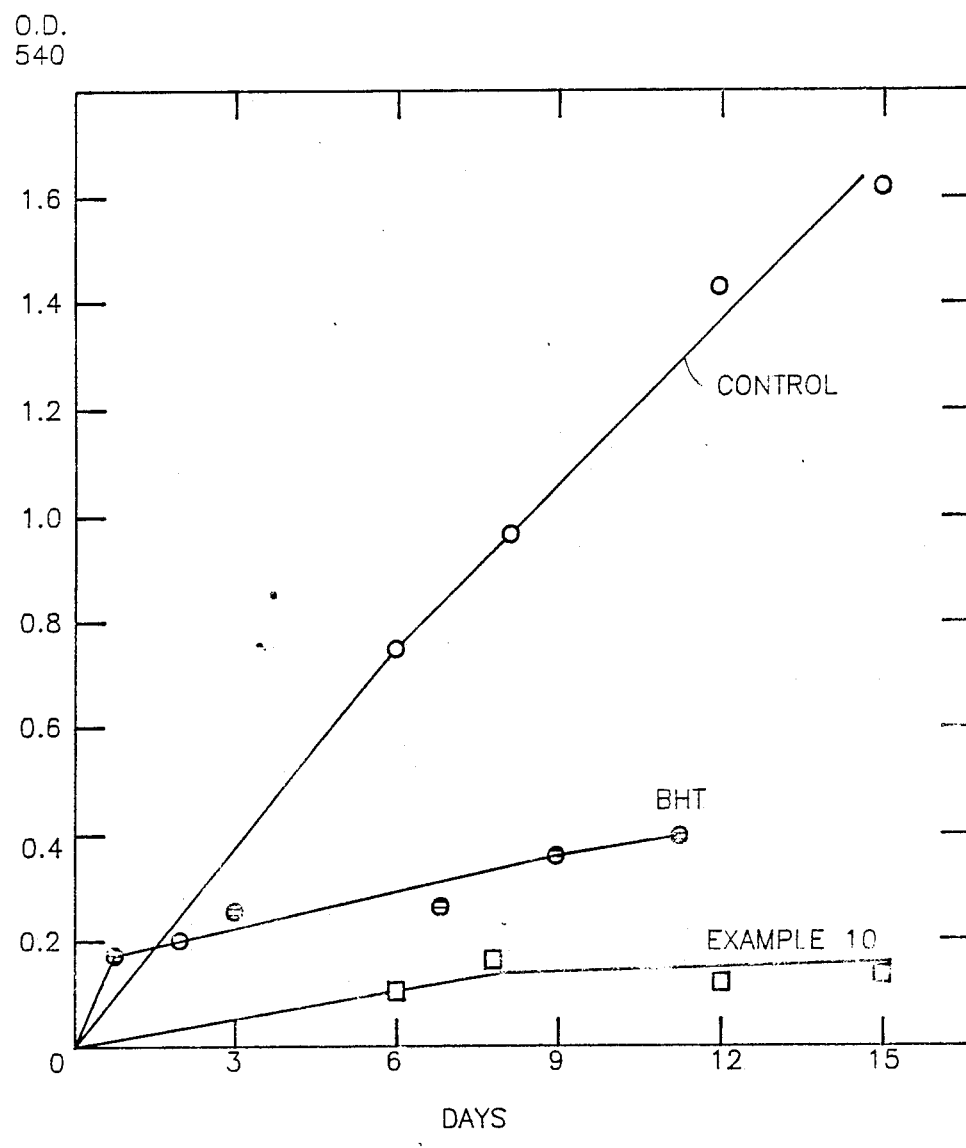
FIG. 2 shows a graphical comparison of the effect of the present antioxidant material with BHT.

The crude antioxidant (A, B and C) was added to linoleic acid to form a mixture containing 20 ml. of $7.5 \times 10^{-3}$M linoleic acid in 0.2M aqueous sodium phosphate buffer (pH 6.5), containing 0.25% Tween 20 (R) and 1 mg. of the crude antioxidant. Controls were run which contained the buffer and Tween 20 but no antioxidant, as well as a sample of linoleic acid with 1 mg. of BHT and the same dispersant system. The mixture was kept at 30° C. and the optical density was determined using the ferric thiocyanate method described by R. B. Koch et al in Arch. Biochem. Biophys. 78:165 (1959). The test results depicted in FIG. 2 show that the antioxidant of the invention is more effective than BHT in preventing oxidation of linoleic acid.

EXAMPLE 10

Isolation of antioxidant materials from clover

A similar procedure to that described for spinach, was applied to isolate antioxidant materials from clover (*trifolium alexandrinum*). The crude extract was separated on Sephadex G-25 to give fractions A, B and C. Fraction A was purified on Ecteola to give fraction $A_1$. Fraction C was resolved on Sephadex G-10 to give fractions $C_1$ and $C_2$. Fraction $C_1$ was further resolved by dissolving in a minimum amount of water, applying to 0.2 mm. silica gel plates and developing in 30:60 v/v $H_2O$-ethanol, to give fractions labelled TLC-1, -2 and -3.

Figure 8:
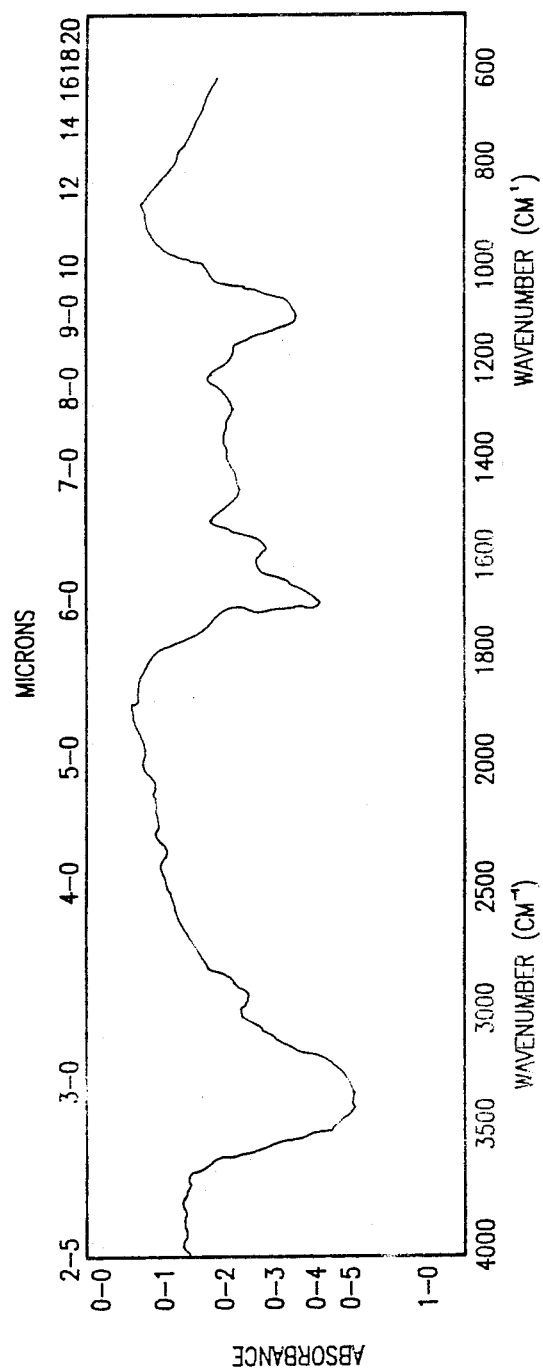
FIG. 8 shows an infrared curve of the present antioxidant material, fraction A, isolated from clover.

The following infrared data was obtained:

A: (see FIG. 8) similar to the analogous spinach fraction

Figure 9:
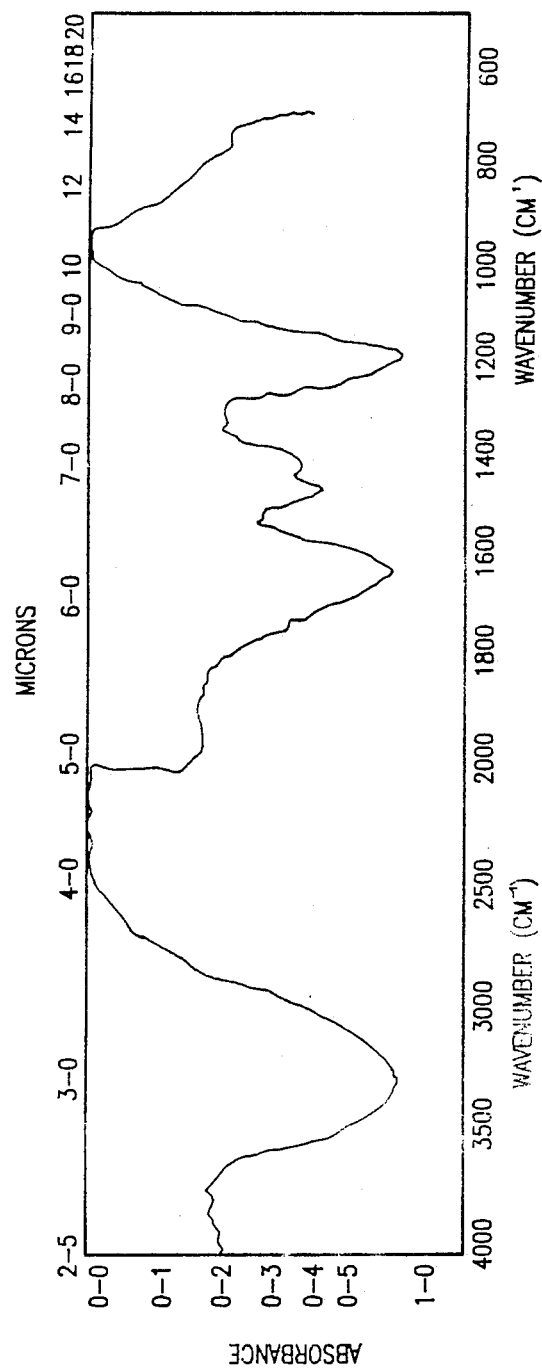
FIG. 9 shows an infrared curve of the present antioxidant material, fraction B, isolated from clover.

B: (see FIG. 9) strong and broad bands at 3300, 1560 and 1130 cm.$^{-1}$, medium band at 1400 cm.$^{-1}$, weak bands at 1350 and 1430 cm.$^{-1}$.

Figure 10:
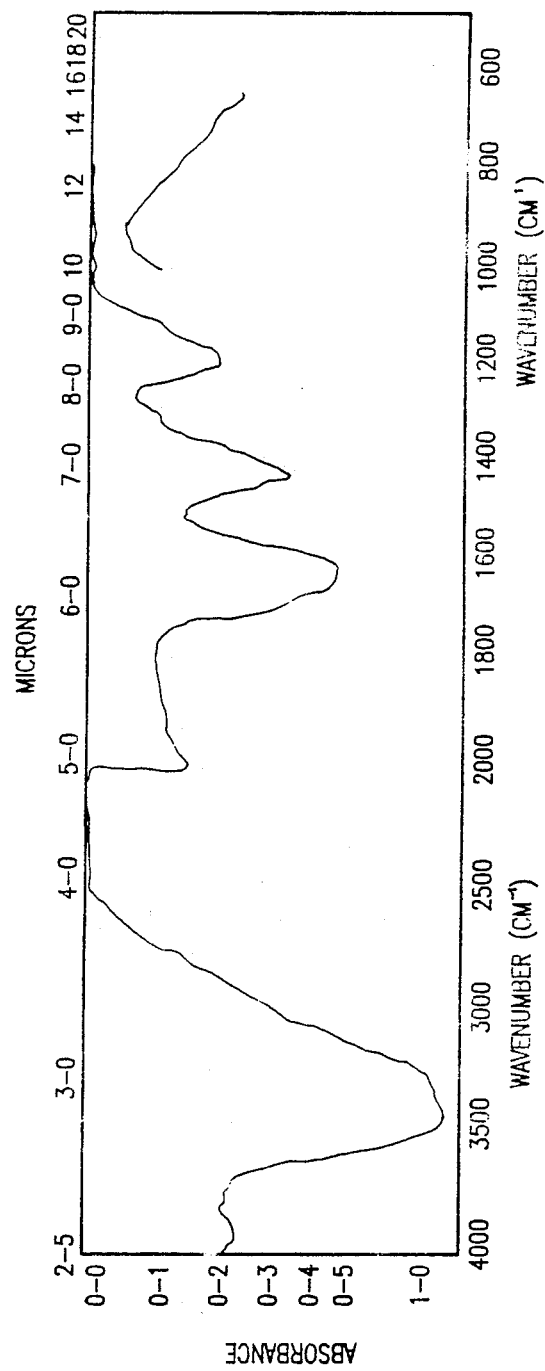
FIG. 10 shows an infrared curve of the present antioxidant material, fraction C, isolated from clover.

C: (see FIG. 10) broad band at 3430 cm.$^{-1}$, strong bands at 1600, 1380 and 1150 cm.$^{-1}$.

Figure 11:
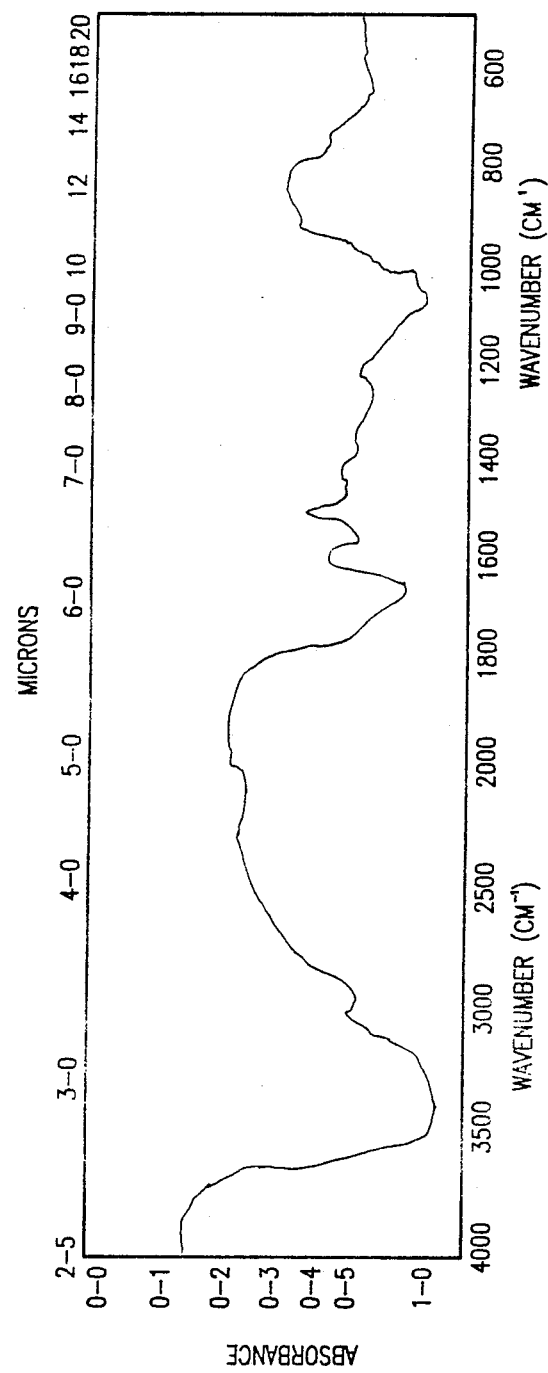
FIG. 11 shows an infrared curve of the present antioxidant material, fraction $A_1$, isolated from clover.

$A_1$: (see FIG. 11) similar to the analogous spinach fraction.

Certain of the foregoing fractions (0.2 mg. in each case) derived from clover were tested as antioxidant in a system which contained linoleic acid as substrate and the enzyme lipoxygenase as catalyst. Oxygen absorption was followed using an oxygen monitor according to Grossman and Zakut, in Methods of Biochemical Analysis (D. Glick, Ed.) 25: 303-29 (1979). The results are shown in Table 7.

TABLE 7

| Inhibition of Lipid Peroxidation by Antioxidants from Clover. | |
|---|---|
| Fraction crude extract | % Inhibition 20 |
| A | 9 |
| B | 16 |
| C | 30 |
| TLC-1 | 42 |
| TLC-3 | 46 |

EXAMPLE 11

Isolation of antioxidant materials from algae

A number of algae samples were homogenized with distilled water and an extract was prepared according to the technique described above for *spinacia oleracea*. The crude homogenate was centrifuged, and the supernatant was collected and dried by lyophilization. The dried crude extracts were tested as antioxidants in a system which contained linoleic acid as a substrate and the enzyme lipoxygenase as catalyst. Oxygen absorption was followed using an oxygen monitor according to Grossman and Zakut, in Methods of Biochemical Analysis (D. Glick, Ed.) 25: 303-29 (1979). The results in Table 8 were obtained using 2.5 mg. crude extract.

TABLE 8

| Inhibition of Lipid Peroxidation by Antioxidants from Algae. | |
|---|---|
| Algae | % Inhibition |
| Spirulina | 30 |
| Nicractinium | 27 |
| Synichococcus | 30 |
| Navicola | 42 |
| Euglena | 35 |
| Red | 35 |

EXAMPLE 12

Rabbits were fed (a) a basal diet deficient in vitamin E, or alternatively (b) the basal diet supplemented with vitamin E or (c) the basal diet supplemented with the present crude antioxidant. After 30 days, it was found that in cases (b) and (c), enzymatic lipid peroxidation was decreased (i.e. both liver microsomal NADPH oxidase and pyruvate oxidase activities were decreased), compared with case (a). Moreover, the endogenous release by isolated aorta segments of prostacyclin ($PGI_2$). detected as 6-keto-$PGF_{1-alpha}$, was significantly increased in cases (b) and (c), as compared with case (a), thus indicating that the present antioxidant may serve as a substitute for vitamin E in food supplements.

EXAMPLE 13

The possibility that the present antioxidant may serve as a substitute for vitamin E was also tested in tissue culture. Fibroblasts were grown in an appropriate medium for three days at a temperature of 37° C., (a) in absence of additive (control), (b) in presence of 0.01% vitamin E, and (c) in presence of 0.01% present (crude) antioxidant. Lipid peroxidation was followed by measuring the level of peroxides after 3 days of incubation. From the results, summarized in Table 9, it is evident that both vitamin E and the present substances react as antioxidants in a similar manner.

| Level of peroxides after 3 days of incubation. | |
|---|---|
| Sample | Peroxide value (TBA assay) |
| (a) | 0.053 |
| (b) | 0.015 |
| (c) | 0.019 |

EXAMPLE 14

COMPARATIVE EFFECTIVENESS OF THE WATER-SOLUBLE ANTIOXIDANT AND ALPHA-TOCOPHERYL ACETATE IN REDUCING THE PEROXIDE LEVEL IN THE SKIN OF EXPERIMENTAL ANIMALS.

In this experiment, alpha-tocopheryl acetate and the present antioxidant were applied to the skin of hairless mice and the level of peroxide in the skin after exposure to UV radiation compared to a control group. The detailed procedure was as follows.

Materials and Methods

The malondialdehyde (MDA) assay is based on the methods of Dixit et al [J. Invest. Derm., 81: 369–75 (1983)], Tappel and Summerfield ["Measurement of and protection from in vivo lipid peroxidation", Free Radicals in Biology Vol. IV (1980). Academic Press, New York (W. A. Pryor, ed.)] and Placer et al [Analytical Biochemistry, 16:359–64 (1966)].

6–8 week old hairless mice [(SKH/Hr); Skin and Cancer Hospital, Temple University, Philadelphia] were anesthetized using a 1:10 dilution of Sodium Pentobarbital (50 mg./ml., Elkins-Sinn. Inc.). The UV light sources were 2 fluorescent lamps (Westinghouse PS-40) and light intensity was measured with an Optometer (United Detector Technology) using a UVB filter. The tissue was homogenized using a Heat Systems model W-10 Sonicator, filtration and centrifugation of the homogenates being effected through a 2.5 micron Millipore filter and a Sorvall RC-5 Speed Centrifuge, respectively. The buffer consisted of 0.1M potassium phosphate, pH 7.4 with $10^{-4}$M magnesium chloride.

The protein assay is based on the method given in Clinical Chemistry, 23: 908 (1977). The modified biuret reagent contains per liter 3.8 g. $CuSO_4$, 6.7 g. EDTA, 17.5 g. glycine, 14.0 g. NaCl and 40.0 g. NaOH. Absorbance was measured on an MS-2 Spectrophotometer (Micromedic Systems, Inc.).

Procedure 20 mice were anesthetized with Sodium Pentobarbital (0.5 mg./10 g. body weight). Two rectangular areas, 6.25 cm.$^2$ each, were outlined on the dorsal and ventral sides of each mouse. The dorsal areas were designated as left dorsal (site A) and right dorsal (site B). The ventral areas were designated as left ventral (site C) and right ventral (site D). The products were applied in an aliquot of 75 ul. to the designated sites. The application protocol was randomized so that a given treatment was not restricted to the same area of the skin. One site on each dorsal and ventral side remained untreated to serve as the irradiated controls. 15 minutes after product application, the mice were exposed to 110 millijoules of UV light per cm.$^2$ of skin area over a period of 220 seconds per side. The mice were placed so that the area to be irradiated was directly under the light source while the areas on the other side were protected from the radiation. The mice were irradiated on both the dorsal and ventral sides. After UV treatment, the mice were returned to separate cages to recover from the anesthesia.

4 hours after irradiation, the mice were sacrificed by cervical dislocation. The skin was removed and stretched over a styrofoam block. The epidermis was separated from the dermis by heating the skin in a water bath for 60 seconds at 54° C. and then scraping the surface with a scalpel. Each 6.25 cm. area of epidermis was placed in a separate 1.5 ml. Eppendorf vial with 200 ul. of buffer. The pieces of epidermis were homogenized by sonication for 2×30 seconds, with a 10 second pause between each 30 second period to prevent heat buildup. The vial was kept in an ice bath.

After homogenization, 1 ml. of buffer was added to each vial and vortexed. The homogenate was filtered through a 2.5 micron filter, twice. An aliquot containing 1.4–1.8 mg. of homogenate protein was placed into test tubes with 0.6 ml. 10% trichloroacetic acid and 1.2 ml. 0.5% (w/v) 2-thiobarbituric acid. The test tube mixture was well vortexed and then placed in a boiling water bath for 10 minutes, the top of the test tube being covered with a marble which acted as a condensor. The tubes were cooled with running tap water and centrifuged for 15 minutes at 30,000×g. Blanks were prepared by placing 0.1M phosphate buffer in test tubes. All assays were done in duplicate.

The level of MDA was determined by reading the color formation with a spectrophotometer at 535 nm. The number of nanmoles MDA produced was equal to $(OD \times Vf)/0.15$, where OD is the optical density at 535 nanometers, Vf is the final volume of the mixture. The amount of MDA produced was standardized to the nanmoles of MDA per mg. of protein. The results were presented in units of nM MDA/mg. protein.

30 ul. of the homogenate blanks were placed in tubes, 3 ml of modified biuret reagent added to each of the tubes which were then vortexed and incubated for 5 minutes at room temperature. The absorbance at 545 nm was measured for each tube. A plot of BSA vs. absorbance was made. The amount of protein in each sample of homogenate was determined based upon the absorbance. The results are shown in Tables 10 and 11. Table 10 (final column) shows the percent decrease in MDA (which is proportional to the decrease in the skin peroxide level) when using 5% alpha-tocopheryl acetate in ethanol. Table 11 gives corresponding figures when using 1% water-soluble antioxidant (the crude product, made as described herein) in Oil of Olay. For a comparison of the effect of the present water-soluble antioxidants in Oil of Olay, with unmodified Oil of Olay control, reference may be made to Examples 3 and 4, above.

TABLE 10

| | 5% alp. tocopheryl acetate in ethanol. | | |
|---|---|---|---|
| | nM MDA/mg. protein | | |
| Sample Number | Untreated Irradiated Site | Treated Irradiated Site | % decrease in MDA by treatment with tocopheryl acetate |
| (DORSAL VALUES) | | | |
| 1 | 0.161 | 0.105 | 34.78 |
| 2 | 0.171 | 0.103 | 39.77 |
| 3 | 0.096 | 0.074 | 22.92 |
| 4 | 0.353 | 0.308 | 12.75 |
| 5 | 0.318 | 0.235 | 26.10 |
| mean | 0.220 | 0.165 | 27.26 |
| S.E. | 0.049 | 0.045 | 4.71 |
| (VENTRAL VALUES) | | | |
| 6 | 0.257 | 0.148 | 42.41 |
| 7 | 0.266 | 0.189 | 28.95 |
| 8 | 0.246 | 0.189 | 23.17 |
| 9 | 0.393 | 0.305 | 22.39 |
| 10 | 0.360 | 0.027 | 25.00 |
| mean | 0.304 | 0.172 | 28.38 |
| S.E. | 0.030 | 0.045 | 3.69 |
| (COMBINED DORSAL AND VENTRAL VALUES) | | | |
| mean | 0.262 | 0.168 | 27.82 |
| S.E. | 0.031 | 0.030 | 2.83 |

TABLE 11

| | 1% water-soluble antioxidant in Oil of Olay. | | |
|---|---|---|---|
| | nM MDA/mg. protein | | |
| Sample Number | Untreated Irradiated Site | Treated Irradiated Site | % decrease in MDA by treatment with tocopheryl acetate |
| (DORSAL VALUES) | | | |
| 1 | 0.240 | 0.141 | 41.25 |
| 2 | 0.367 | 0.258 | 29.70 |
| 3 | 0.237 | 0.125 | 47.26 |
| 4 | 0.309 | 0.182 | 41.10 |
| 5 | 0.281 | 0.208 | 25.98 |
| mean | 0.287 | 0.183 | 37.06 |
| S.E. | 0.024 | 0.024 | 3.97 |
| (VENTRAL VALUES) | | | |
| 6 | 0.135 | 0.062 | 54.07 |
| 7 | 0.396 | 0.259 | 34.60 |
| 8 | 0.217 | 0.126 | 41.94 |
| 9 | 0.337 | 0.230 | 31.75 |
| 10 | 0.390 | 0.251 | 35.64 |
| mean | 0.295 | 0.186 | 39.60 |
| S.E. | 0.051 | 0.039 | 3.98 |
| (COMBINED DORSAL AND VENTRAL VALUES) | | | |
| mean | 0.291 | 0.184 | 38.33 |
| S.E. | 0.027 | 0.022 | 2.68 |

Conclusions

The foregoing data show that the present water-soluble antioxidant (1%, Oil of Olay) is very effective in reducing the level of peroxides in the skin of nude mice and that alphatocopheryl acetate (5% in ethanol) is significantly less effective for this purpose.

EXAMPLE 15

The ability of the water-soluble antioxidants to inhibit oxidative deterioration in foodstuffs is demonstrated in two food preservation systems. The significance of these experiments in relation to the present invention is that if these antioxidants are used in place of vitamin E, in order to impart an in vivo biological effect in the body, then there need be little fear that foodstuffs in which they may be used might deteriorate prior to use. As has been stated above, it is well within the competence of one skilled in the art to determine the amount of the water-soluble antioxidant to be added to an oxidation-prone foodstuff not merely to inhibit oxidation thereof for a given period of time e.g. for the storage and/or shelf-life of the foodstuff (which mere inhibition of oxidation does not fall within the scope of the present invention), but also to determine the amount of the water-soluble antioxidant to be added to such an oxidation-prone foodstuff, so that it will additionally act as an effective in vivo biological antioxidant, in accordance with the present invention.

Tables 12 and 13 show the effectiveness of the water-soluble antioxidant in inhibiting the formation of peroxides in potato chips and in ground meat, respectively.

| Level of peroxides in potato chips. | | | |
|---|---|---|---|
| Potato chips were fried in soybean oil with and without 0.1% water-soluble antioxidant (crude product). For this purpose the antioxidant was dissolved in a little detergent. | | | |
| Time | Sample | Peroxide value | %* |
| 0 weeks | 0.1% antioxidant | 0.045 | 100 |
| | control | 0.050 | 111 |
| 4 weeks | 0.1% antioxidant | 0.053 | 117 |
| | control | 0.190 | 422 |

*the level of antioxidant-containing sample at zero time = 100%

| Level of peroxides in ground meat. | | |
|---|---|---|
| Water-soluble antioxidant (crude product) was dissolved in water and added to ground meat which was kept frozen. | | |
| Time (weeks) | Sample (ppm antioxidant) | Peroxide value (OD at 350 nm) |
| 0 | 0 | 0.200 |
| | 200 | 0.210 |
| | 400 | 0.205 |
| 4 weeks | 0 | 0.441 |
| | 200 | 0.236 |

-continued

Level of peroxides in ground meat.
Water-soluble antioxidant (crude product) was dissolved
in water and added to ground meat which was kept frozen.

| Time (weeks) | Sample (ppm antioxidant) | Peroxide value (OD at 350 nm) |
|---|---|---|
|  | 400 | 0.204 |
| 8 weeks | 0 | 0.500 |
|  | 200 | 0.190 |
|  | 400 | 0.250 |

While the invention has been described above with respect to its presently preferred embodiments, it will be apparent to those skilled in the art that many variations and modifications may be made. The invention is accordingly not to be construed as restricted to the illustrated embodiments, rather its scope will be defined in the claims which follow.

We claim:

1. A food supplement which comprises in combination (i) as an essential antioxidant ingredient, a material which is stable for an extended period of time, at least in the dry state, under ambient conditions, said material being selected from the group consisting of water-soluble extracts prepared by aqueous extraction of plant tissue selected from leaf and stem tissue and fractions separable from said extracts by chromatography, provided that antioxidant activity is identifiable in said material and that the latter is present in an antioxidant effective amount and (ii) an orally ingestible diluent or carrier, said tissue having been obtained from at least one plant selected from the group consisting of (A) member of the plant families Aizoceae, Amarathaceae, Caryophyllaceae, Chenopodiaceae except Spinacia, Nyctaginaceae, Phytolaccaeae, Portulacaceae and (B) Spinacia, Trifolium, Medicago, Zea, Nicotiana, Pennisetum and Allium.

2. A food supplement according to claim 1, wherein said extracts are chromatographically separable on dextran which has been cross-linked with epichlorohydrin and has a pore size of 50–150 μm, into fractions which are colored brown (A), yellow (B) and orange (C), and of which fraction A is chromatographically purifiable on a substance selected from the group consisting of:

a condensation product of cellulose with epichlorohydrin and triethanolamine having a capacity of 0.3 to 0.4 meq./g. and a particle size of 0.05–0.2 mm., and dextran which has been cross-linked with epichlorohydrin and has a pore size of 40–120 μm; to give a fraction ($A_1$) having an infrared spectrum with substantially the following features, namely, broad band at 3300–3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$, and of which fractions, fraction C is chromatographically separable on dextran which has been cross-linked with epichlorohydrin and has a pore size of 40–120 μm, into fractions colored dark brown ($C_1$) and yellow orange ($C_2$).

3. A food supplement which comprises in combination (i) as an essential active antioxidant ingredient, a material characterized by stability for an extended period of time, at least in the dry state, under ambient conditions, said material being at least one of the fractions selected from the group consisting of fractions A, $A_1$, B, $C_1$ and $C_2$, as defined in claim 2, and (iii) an orally ingestible diluent or carrier.

4. A food supplement according to claim 3, wherein said material comprises a combination of at least two substances selected from said fractions A, $A_1$, B, $C_1$ and $C_2$.

5. A food supplement according to claim 1, further characterized by the fact that said plant tissue is comminuted, and extraction has been effected at a temperature within the range of from about 4° to about 100° C.

6. A food supplement according to claim 5, wherein said temperature is about 25° C.

7. A food supplement according to claim 1, further characterized by the fact that extraction has been effected by boiling said plant tissue with water.

8. A food supplement according to claim 1, wherein said material is selected from the group consisting of chromatographic fractions identified by the labels (a), (b), (c), (d), (e), (f) and (g), said fractions being respectively characterized by an infrared spectrum with substantially the following features:

(a) broad band at 3400 cm.$^{-1}$, strong bands at 1050 and 1650 cm.$^{-1}$, weak bands at 1250 and 1430 cm.$^{-1}$;

(b) broad bands at 3400, 1640 and 1080 cm.$^{-1}$, additional bands at 1420, 1300 and 810 cm.$^{-1}$;

(c) broad bands at 3400 and 1600 cm.$^{-1}$, strong band at 1390 cm.$^{-1}$, additional bands at 1070 and 820 cm.$^{-1}$;

(d) broad band at 3300 cm.$^{-1}$, strong band at 1620 cm.$^{-1}$, additional bands at 1390, 1320, 1080 and 770 cm.$^{-1}$;

broad band at 3300–3400 cm.$^{-1}$, strong band at 1650 cm.$^{-1}$, additional bands at 1730, 1540, 1250 and 1080 cm.$^{-1}$, weak bands at 2920, 1400 and 1150 cm.$^{-1}$;

(f) strong and broad bands at 3300, 1560 and 1130 cm.$^{-1}$, medium band at 1400 cm.$^{-1}$, weak bands at 1350 and 1430 cm.$^{-1}$;

(g) broad band at 3430 cm.$^{-1}$, strong bands at 1600, 1380 and 1150 cm.$^{-1}$.

9. A food supplement according to claim 1, wherein said orally ingestible diluent or carrier comprises a substance selected from the group consisting of a manufactured cereal, a fruit or vegetable product, a beverage or beverage concentrate, a ground meat product or a vegetable analogue thereof, and any inert diluent, carrier or excipient known in the pharmaceutical art.

10. A food supplement according to claim 9, which comprises at least one additional ingredient selected from the group consisting of (a) the water-soluble vitamins thiamine, riboflavin, niacin, pyridoxine, pantothenic acid, biotin, folic acid, cobalamin and ascorbic acid, (b) the oil-soluble vitamins retinol, calciferol, tocopherol and menadione, (c) in combined form the elements sodium, potassium, calcium, phosphorus, magnesium, chlorine and sulfur, iron, copper, iodine, manganese, cobalt, zinc molybdenum, fluorine, selenium and chromium, (d) unsaturated fatty acids which are known to metabolized in the body to prostaglandins, and physiologically compatible derivatives of said fatty acids, and (e) acceptable dispersing and suspending agents, and water.

11. A food supplement according to claim 10, which is in the form of a powder, tablet, capsule, solution, concentrate, syrup, suspension or dispersion.

12. A food supplement according to claim 9, which is in the form of a powder, tablet, capsule, solution, concentrate, syrup, suspension or dispersion.

13. A food supplement according to claim 1, wherein said orally ingestible diluent or carrier comprises a substance selected from the group consisting of a manufactured cereal, a fruit or vegetable product, a beverage or beverage concentrate, a ground meat product or a vegetable analogue thereof, and any inert diluent, carrier or excipient known in the pharmaceutical art, and said antioxidant ingredient constitutes about 0.001 to about 1.0% by weight of the food supplement.

14. A food supplement according to claim 13, which comprises at least one additional ingredient selected from the group consisting of (a) the water-soluble vitamins thiamine, riboflavin, niacin, pyridoxine, pantothenic acid, biotin, folic acid, cobalamin and ascorbic acid, (b) the oil-soluble vitamins retinol, calciferol, tocopherol and menadione, (c) in combined form the elements sodium, potassium, calcium, phosphorus, magnesium, chlorine; sulfur, iron, copper, iodine, manganese, cobalt, zinc, molybdenum, fluorine, selenium and chromium, (d) unsaturated fatty acids which are known to be metabolized in the body to prostaglandins, and physiologically compatible derivatives of said fatty acids, and (e) acceptable dispersing and suspending agents, and water.

15. A food supplement according to claim 14, which is in the form of a powder, tablet, capsule, solution, concentrate, syrup, suspension or dispersion.

16. A food supplement according to claim 13, which is in the form of a powder, tablet, capsule, solution, concentrate, syrup, suspension or dispersion.

17. A food supplement according to claim 13, wherein said antioxidant ingredient constitutes about 0.005 to about 0.1% by weight of the food supplement.

18. A food supplement according to claim 1 which is further characterized by the fact that said tissue is obtained from at least one plant selected from the group consisting of members of the plant families Aizoaceae, Amaranthaceae, Caryophyllaceae, Chenopodiaceae except Spinacia, Nyctaginaceae, Phytolaccaeae and Portulacaceae.

19. A food supplement according to claim 18, wherein said tissue is obtained from a plant of families selected from the group consisting of Chenopodiaceae except Spinacia, and Aizoaceae.

20. A food supplement according to claim 19, wherein said tissue is obtained from a plant of the group consisting of Atriplex, Beta and Tetragonia.

21. A food supplement according to claim 1 which is further characterized by the fact that said tissue is obtained from a plant of the group consisting of Spinacia, Trifolium, Medicago, Zea, Nicotiana, Pennisetum, and Allium.

* * * * *